(12) United States Patent
Okamoto et al.

(10) Patent No.: US 11,299,448 B2
(45) Date of Patent: Apr. 12, 2022

(54) ACTIVE ESTER COMPOUND

(71) Applicant: DIC Corporation, Tokyo (JP)

(72) Inventors: Tatsuya Okamoto, Ichihara (JP); Yutaka Satou, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days.

(21) Appl. No.: 16/610,582

(22) PCT Filed: Apr. 10, 2018

(86) PCT No.: PCT/JP2018/015021
§ 371 (c)(1),
(2) Date: Nov. 4, 2019

(87) PCT Pub. No.: WO2018/207532
PCT Pub. Date: Nov. 15, 2018

(65) Prior Publication Data
US 2020/0148618 A1    May 14, 2020

(30) Foreign Application Priority Data

May 12, 2017 (JP) .............................. JP2017-095626

(51) Int. Cl.
| C07C 65/21 | (2006.01) |
| C07C 67/03 | (2006.01) |
| C08L 27/12 | (2006.01) |
| H01L 23/29 | (2006.01) |
| H05K 1/03  | (2006.01) |
| C08K 5/10  | (2006.01) |

(52) U.S. Cl.
CPC .............. C07C 65/21 (2013.01); C07C 67/03 (2013.01); C08L 27/12 (2013.01); H01L 23/29 (2013.01); H05K 1/03 (2013.01); C08K 5/10 (2013.01)

(58) Field of Classification Search
None
See application file for complete search history.

(56) References Cited

U.S. PATENT DOCUMENTS 3,824,211 A    7/1974    Howerton

FOREIGN PATENT DOCUMENTS

| JP | H03-246243 A | 11/1991 |
| JP | H08-006270 A | 1/1996 |
| JP | H08-019023 B2 | 2/1996 |
| JP | H08-217863 A | 8/1996 |
| JP | 2005-164651 A | 6/2005 |
| JP | 2011-256300 A | 12/2011 |
| JP | 2016-141701 A | 8/2016 |

OTHER PUBLICATIONS

Vygodskii, Ya. S et al., "Effect of poly (heteroarylenes) with different molecular weights on free-radical polymerization of methyl methacrylate", Vysokomolekulyamye Soedineniya, Seriya A i Seriya B, (2002), 44 (12), pp. 2096-2102 (in particular, p. 2099, V of right column.
Babuchkina T. A. et al., "Nuclear quadrupole resonance in polymers", Journal of Molecular Structure, (1984), 117 (3-4), pp. 323-328 (in particular, p. 325, "VIII" of table 1).
International Search Report dated Jul. 17, 2018, issued for PCT/JP2018/015021.
Peng Wei et al., "The influence of bisphenol AF unit on thermal behavior of thermotropic liquid crystal copolyesters", Thermochimica Acta, 2014, 586, pp. 45-51.

*Primary Examiner* — Sudhakar Katakam
*Assistant Examiner* — Jennifer C Sawyer
(74) *Attorney, Agent, or Firm* — Locke Lord LLP; James E. Armstrong, IV; Nicholas J. DiCeglie, Jr.

(57) ABSTRACT

An active ester compound that can form a cured product having excellent dielectric properties and copper foil adhesion properties is provided, a curable composition including the active ester compound is provided, and a cured product of the curable composition is provided. Also provided are a semiconductor encapsulating material, a printed wiring board, and a build-up film formed by using the curable composition. Specifically, an active ester compound is provided which includes a fluorinated hydrocarbon structural moiety and a plurality of aromatic ester structural moieties in the structure of the molecule and includes an aryloxycarbonyl structure or an arylcarbonyloxy structure at an end of the molecule, a curable composition including the active ester compound, and a cured product of the curable composition, and also provided are a semiconductor encapsulation material, a printed wiring board, and a build-up film formed by using the curable composition.

9 Claims, 1 Drawing Sheet

ACTIVE ESTER COMPOUND

TECHNICAL FIELD

The present invention relates to an active ester compound that can form a cured product having excellent dielectric properties and copper foil adhesion properties and also relates to a curable composition including the active ester compound and to a cured product of the curable composition. In addition, the present invention relates to a semiconductor encapsulating material, a printed wiring board, and a build-up film formed by using the curable composition.

BACKGROUND ART

Various electronic components are becoming thinner and smaller, and accordingly, in the technical field of insulating materials that are used for semiconductors, multilayer printed boards, and the like, there is a need to develop a new resin material that responds to market trends. Specifically, it is required that resulting cured products have a thermal resistance, a moisture absorption resistance, and a copper foil adhesion property, as a matter of course. Other important requirements are, for example, as follows: resulting cured products have a low dielectric constant value and a low dielectric loss tangent value, which are required for increased signal speed and frequency; resulting cured products have high-temperature reliability, that is, have a property of not undergoing changes in physical properties, such as a glass transition temperature (Tg); and a cure shrinkage factor and a coefficient of linear expansion are low, which is required to inhibit warping and distortion attributable to reduced thicknesses.

A resin material that can form a cured product having excellent dielectric properties is known. The resin composition is made of a base resin, which includes a polytetrafluoroethylene dispersion and an epoxy resin, and an acid anhydride curing agent (see PTL 1, listed below). The epoxy resin composition described in PTL 1 was formulated to include a polytetrafluoroethylene dispersion to reduce the dielectric constant and dielectric loss tangent values. However, sufficient adhesion properties with respect to copper foils were not achieved, and, therefore, the epoxy resin composition could not be used for fine interconnections, which accompanied the miniaturization of electronic components.

CITATION LIST

Patent Literature

PTL 1: Japanese Unexamined Patent Application Publication No. 2016-141701

SUMMARY OF INVENTION

Technical Problem

Accordingly, objects of the present invention are to provide an active ester compound that can form a cured product having excellent dielectric properties and copper foil adhesion properties, to provide a curable composition including the active ester compound, to provide a cured product of the curable composition, and to provide a semiconductor encapsulating material, a printed wiring board, and a build-up film formed by using the curable composition.

Solution to Problem

The present inventors diligently performed studies to achieve the object described above and found the following. An active ester compound including a fluorinated hydrocarbon structural moiety and a plurality of aromatic ester structural moieties in the structure of the molecule and including an aryloxycarbonyl structure or an arylcarbonyloxy structure at an end of the molecule can form a cured product having excellent dielectric properties and high adhesion properties with respect to copper foils, and, therefore, the active ester compound has a high utility value for serving as, for example, a curing agent for epoxy resins for electronic components. Accordingly, the present inventors completed the present invention.

Specifically, the present invention relates to an active ester compound including a fluorinated hydrocarbon structural moiety (F) and a plurality of aromatic ester structural moieties (E) in a structure of a molecule and including an aryloxycarbonyl structure (P) or an arylcarbonyloxy structure (A) at an end of the molecule.

The present invention further relates to a curable composition including the active ester compound and a curing agent.

The present invention further relates to a curable composition including the active ester compound, a curing agent, and a poly(fluoroalkylene) resin.

The present invention further relates to a cured product of the curable composition.

The present invention further relates to a semiconductor encapsulating material including the curable composition.

The present invention further relates to a printed wiring board including a product of the curable composition.

Advantageous Effects of Invention

With the present invention, an active ester compound that can form a cured product having excellent dielectric properties and copper foil adhesion properties, a curable composition including the active ester compound, and a cured product of the curable composition are provided, and also, a semiconductor encapsulating material, a printed wiring board, and a build-up film formed by using the curable composition are provided.

DESCRIPTION OF EMBODIMENTS

Figure 1:
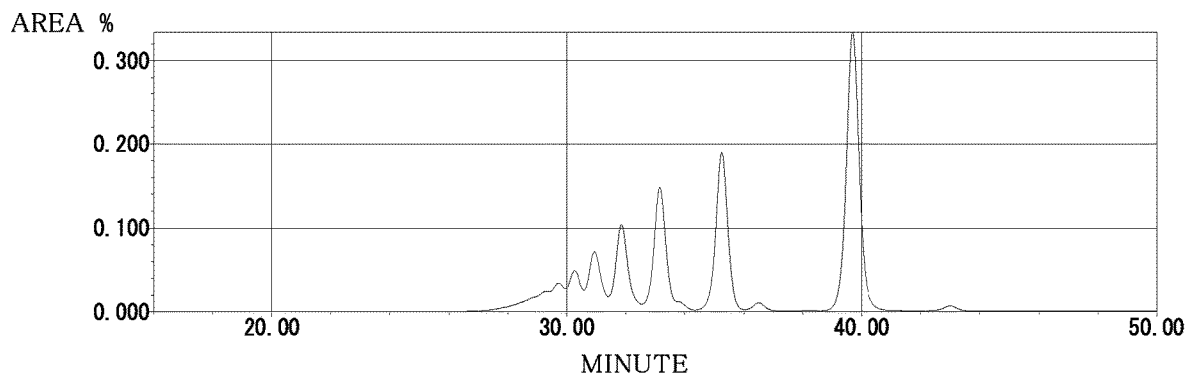
FIG. 1 is a GPC chart of an active ester compound (1), which was obtained in Example 1.

The present invention will now be described in detail.
According to the present invention, an active ester compound includes a fluorinated hydrocarbon structural moiety (F) and a plurality of aromatic ester structural moieties (E) in the structure of the molecule and includes an aryloxycarbonyl structure (P) or an arylcarbonyloxy structure (A) at an end of the molecule.

The fluorinated hydrocarbon structural moiety (F) is a structure of a hydrocarbon group in which one or more or all of the hydrogen atoms are substituted with fluorine atoms. Examples of the hydrocarbon group include aliphatic hydrocarbon groups, alicyclic-structure-containing hydrocarbon groups, and aromatic-ring-containing hydrocarbon groups. The aliphatic hydrocarbon group may be linear or branched and may have one or more unsaturated bonds. Furthermore, the aliphatic hydrocarbon group may be a monovalent hydrocarbon group, such as an alkyl group, or may be a divalent hydrocarbon group, such as an alkylene group. The alkylene group may be a structural moiety in which a plurality of alkylene groups are linked to one another via an oxygen atom, a sulfur atom, a carbonyl group, a sulfonyl group, an ester linkage, or the like. Examples of such a structural moiety include (poly)oxyalkylene structures.

Examples of alicyclic structures that may be present in the alicyclic-structure-containing hydrocarbon group include cyclopentane structures, cyclohexane structures, norbornane structures, norbornene structures, tricyclodecane structures, dicyclopentadiene structures, and adamantane structures. The alicyclic-structure-containing hydrocarbon group may include, in addition to the alicyclic structure, one or more structural moieties, examples of which include alkyl groups and alkylene groups. Furthermore, the alicyclic-structure-containing hydrocarbon group may be a monovalent hydrocarbon group, such as a cycloalkyl group, or may be a divalent hydrocarbon group, such as a cycloalkylene group.

Examples of aromatic ring structures that may be present in the aromatic-ring-containing hydrocarbon group include benzene rings, naphthalene rings, and anthracene rings. The aromatic-ring-containing hydrocarbon group may include, in addition to the aromatic ring structure, one or more structural moieties, examples of which include alkyl groups and alkylene groups. Furthermore, the aromatic-ring-containing hydrocarbon group may be a monovalent hydrocarbon group, such as an aryl group or an aralkyl group, or may be a divalent hydrocarbon group, such as an arylene group or a dialkylene arene.

In the active ester compound of the present invention, the fluorinated hydrocarbon structural moiety (F) is one or more fluorinated hydrocarbon structural moieties (F). When two or more fluorinated hydrocarbon structural moieties (F) are present, the structural moieties may be the same as or different from each other. In particular, in terms of providing an active ester compound having enhanced copper foil adhesion properties, it is preferable that the hydrocarbon structure of the fluorinated hydrocarbon structural moiety (F) be an aliphatic hydrocarbon group, which is preferably an alkyl group having 1 to 6 carbon atoms. Further, a perfluoroalkyl group having 1 to 6 carbon atoms is preferable.

The aromatic ester structural moiety (E) is a moiety containing an ester linkage formed from a hydroxyl group bound to an aromatic ring and a carboxyl group bound to an aromatic ring. The aromatic ester structural moiety (E) has high activity for reaction with a curing agent, such as an epoxy resin.

A specific example of the aryloxycarbonyl structure (P) is a structural moiety represented by structural formula (1) below. Furthermore, a specific example of the arylcarbonyloxy structure (A) is a structural moiety represented by structural formula (2) below.

[Chem. 1]

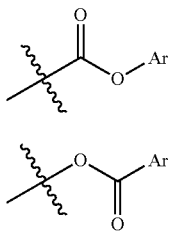

(1)

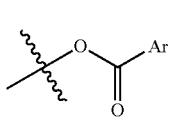

(2)

[In the formula, Ar is an aromatic ring, which may contain a substituent group.]

In structural formulae (1) and (2), Ar represents an aromatic ring. Specific examples include benzene rings, naphthalene rings, and anthracene rings. In particular, a naphthalene ring is preferable in terms of providing an active ester compound that can form a cured product having excellent properties and which has good miscibility with a curing agent and other resin components.

Examples of one or more substituent groups on the aromatic nucleus include aliphatic hydrocarbon groups, alkoxy groups, halogen atoms, aryl groups, aryloxy groups, and aralkyl groups, in addition to the fluorinated hydrocarbon structural moiety (F). The aliphatic hydrocarbon groups may be linear or branched and may have an unsaturated bond in the structure. Specific examples include methyl groups, ethyl groups, propyl groups, butyl groups, pentyl groups, hexyl groups, cyclohexyl groups, heptyl groups, octyl groups, and nonyl groups. Examples of the alkoxy groups include methoxy groups, ethoxy groups, propyloxy groups, and butoxy groups. Examples of the halogen atoms include a fluorine atom, a chlorine atom, and a bromine atom. Examples of the aryl groups include phenyl groups, naphthyl groups, anthryl groups, and structural moieties including one or more of these and in which a substituent is present on the aromatic nucleus thereof, the substituent being an aliphatic hydrocarbon group, an alkoxy group, a halogen atom, or the like. Examples of the aryloxy groups include phenyloxy groups, naphthyloxy groups, anthryloxy groups, and structural moieties including one or more of these and in which a substituent is present on the aromatic nucleus thereof, the substituent being an alkyl group, an alkoxy group, a halogen atom, or the like. Examples of the aralkyl groups include benzyl groups, phenylethyl groups, naphthylmethyl groups, naphthylethyl groups, and structural moieties including one or more of these and in which a substituent is present on the aromatic nucleus thereof, the substituent being an alkyl group, an alkoxy group, a halogen atom, or the like.

The active ester compound of the present invention includes the fluorinated hydrocarbon structural moiety (F) and the plurality of aromatic ester structural moieties (E) in the structure of the molecule and includes an aryloxycarbonyl structure (P) or an arylcarbonyloxy structure (A) at an end of the molecule. As long as these structural moieties and structure are present, other specific structures are not particularly limited, and any of a variety of structures may be included. Furthermore, the molecular weight of the active ester compound is also not particularly limited. The active ester compound may be a compound having a single molecular weight or an oligomer or a polymer having a molecular weight distribution. Specific examples of the active ester compound include the following (A1) to (A4).

Note that these are merely examples of the active ester compound and that the active ester compound of the present invention is not limited to the examples. Furthermore, the active ester compounds may be used alone or in a combination of two or more.

Active ester compound (A1): an active ester compound that is an esterification product of a compound (a1) and a compound (a2), at least one of the compounds (a1) and (a2) having the fluorinated hydrocarbon structural moiety (F) in the structure of the molecule, the compound (a1) being an aromatic monohydroxy compound, the compound (a2) being an aromatic polycarboxylic acid or an acid halide thereof Active ester compound (A2): an active ester compound that is an esterification product of a compound (a3) and a compound (a4), at least one of the compounds (a3) and (a4) having the fluorinated hydrocarbon structural moiety (F) in the structure of the molecule, the compound (a3) being a compound containing two or more phenolic hydroxyl groups in the structure of the molecule, the compound (a4) being an aromatic monocarboxylic acid or an acid halide thereof Active ester compound (A3): an active ester compound that is an esterification product of a compound (a1), a compound (a2), and a compound (a3), at least one of the compounds (a1), (a2), and (a3) having the fluorinated hydrocarbon structural moiety (F) in the structure of the molecule, the compound (a1) being an aromatic monohydroxy compound, the compound (a2) being an aromatic polycarboxylic acid or an acid halide thereof, the compound (a3) being a compound containing two or more phenolic hydroxyl groups in the structure of the molecule Active ester compound (A4): an active ester compound that is an esterification product of a compound (a2), a compound (a3), and a compound (a4), at least one of the compounds (a2), (a3), and (a4) having the fluorinated hydrocarbon structural moiety (F) in the structure of the molecule, the compound (a2) being an aromatic polycarboxylic acid or an acid halide thereof, the compound (a3) being a compound containing two or more phenolic hydroxyl groups in the structure of the molecule, the compound (a4) being an aromatic monocarboxylic acid or an acid halide thereof.

Specific examples of the aromatic monohydroxy compound (a1) include phenol and phenolic compounds in which one or more substituent groups are present on the aromatic nucleus of a phenol; naphthol and naphthol compounds in which one or more substituent groups are present on the aromatic nucleus of a naphthol; and anthracenol and anthracenol compounds in which one or more substituent groups are present on the aromatic nucleus of an anthracenol. Examples of the substituent group on the aromatic nucleus include the fluorinated hydrocarbon structural moiety (F), aliphatic hydrocarbon groups, alkoxy groups, halogen atoms, aryl groups, aryloxy groups, and aralkyl groups. Specific examples of these are as described above. The aromatic monohydroxy compounds (a1) may be used alone or in a combination of two or more.

In particular, a phenolic compound or a naphthol compound is preferable, and phenol, naphthol, or a compound in which one or two substituent groups as described above are present on the aromatic nucleus of a phenol or a naphthol is more preferable, in terms of providing an active ester compound that can form a cured product having excellent dielectric properties and copper foil adhesion properties and also being excellent in thermal resistance and other properties. It is preferable that the substituent group on the aromatic nucleus be the fluorinated hydrocarbon structural moiety (F) or an aliphatic hydrocarbon group or an aralkyl group having 1 to 6 carbon atoms.

Examples of the aromatic polycarboxylic acid or an acid halide thereof (a2) include benzenedicarboxylic acids, such as isophthalic acid and terephthalic acid; benzenetricarboxylic acids, such as trimellitic acid; naphthalene dicarboxylic acids, such as naphthalene-1,4-dicarboxylic acid, naphthalene-2,3-dicarboxylic acid, naphthalene-2,6-dicarboxylic acid, and naphthalene-2, 7-dicarboxylic acid; acid halides thereof; and compounds including one or more of these and in which one or more substituent groups are present on the aromatic nucleus thereof. Examples of the acid halides include acid chlorides, acid bromides, acid fluorides, and acid iodides. Furthermore, examples of the substituent group on the aromatic nucleus include the fluorinated hydrocarbon structural moiety (F), aliphatic hydrocarbon groups, alkoxy groups, halogen atoms, aryl groups, aryloxy groups, and aralkyl groups. Specific examples of these are as described above. The aromatic polycarboxylic acids or acid halides thereof (a2) may be used alone or in a combination of two or more. In particular, a benzenedicarboxylic acid, such as isophthalic acid or terephthalic acid, or an acid halide thereof is preferable in terms of providing an active ester compound that can form a cured product having excellent dielectric properties and copper foil adhesion properties and also being excellent in thermal resistance and other properties.

Examples of the compound containing two or more phenolic hydroxyl groups in the structure of the molecule (a3) include various aromatic polyhydroxy compounds, novolac resins formed from one or more reaction raw materials that include one or more of the aromatic monohydroxy compounds (a1), and reaction products of reaction raw materials that essentially include the following: one or more of the aromatic monohydroxy compounds (a1); and a compound (X) represented by one of the following structural formulae, (x-1) to (x-5).

[Chem. 2]

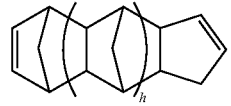
(x-1)

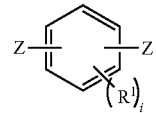
(x-2)

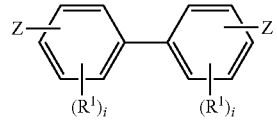
(x-3)

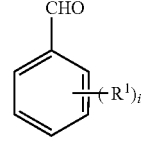
(x-4)

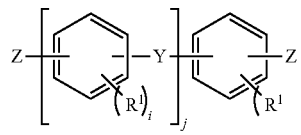

(x-5)

[In the formulae, h is 0 or 1; each of $R^1$ is independently the fluorinated hydrocarbon structural moiety (F), an aliphatic hydrocarbon group, an alkoxy group, a halogen atom, an aryl group, an aryloxy group, or an aralkyl group; i is an integer of 0 or 1 to 4; Z is a vinyl group, a halomethyl group, a hydroxymethyl group, or an alkyloxymethyl group; Y is an alkylene group having 1 to 4 carbon atoms, an oxygen atom, a sulfur atom, or a carbonyl group; and j is an integer of 1 to 4.]

Examples of the various aromatic polyhydroxy compounds include dihydroxybenzene, trihydroxybenzene, tetrahydroxybenzene, dihydroxynaphthalene, trihydroxynaphthalene, tetrahydroxynaphthalene, dihydroxyanthracene, trihydroxyanthracene, tetrahydroxyanthracene, polyhydroxybiphenyls, poly(hydroxyphenyl)alkanes, other bisphenol compounds, and compounds including one or more of these compounds and in which one or more substituent groups are present on one or more carbon atoms. Examples of the substituent groups on one or more carbon atoms include the fluorinated hydrocarbon structural moiety (F), aliphatic hydrocarbon groups, alkoxy groups, halogen atoms, aryl groups, aryloxy groups, and aralkyl groups. Specific examples of these are as described above.

With regard to $R^1$ in structural formulae (x-1) to (x-5), specific examples of the fluorinated hydrocarbon structural moiety (F), the aliphatic hydrocarbon group, the alkoxy group, the halogen atom, the aryl group, the aryloxy group, and the aralkyl group are as described above. Furthermore, a reaction between the aromatic monohydroxy compound (a1) and the compound (x) can be carried out by heating and stirring at a temperature of approximately 80 to 180° C. in the presence of an acidic catalyst.

The compounds containing two or more phenolic hydroxyl groups in the structure of the molecule (a3) may be used alone or in a combination of two or more. In particular, a bis(hydroxyphenyl)fluorinated alkane represented by structural formula (3) below is preferable in terms of providing an active ester compound that can form a cured product having excellent dielectric properties and copper foil adhesion properties and also being excellent in thermal resistance and other properties.

[Chem. 3]

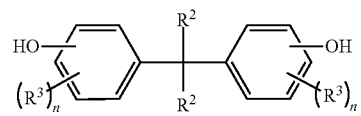

(3)

[In the formula, each of $R^2$ is independently a fluorinated aliphatic hydrocarbon group; $R^3$ is the fluorinated hydrocarbon structural moiety (F), an aliphatic hydrocarbon group, an alkoxy group, a halogen atom, an aryl group, an aryloxy group, or an aralkyl group; and n is an integer of 0 or 1 to 4.]

With regard to $R^2$ in structural formula (1), the aliphatic hydrocarbon group may be linear or branched and may have an unsaturated bond in the structure. In particular, it is preferable that the aliphatic hydrocarbon group be an alkyl group having 1 to 6 carbon atoms.

Examples of the aromatic monocarboxylic acid or an acid halide thereof (a4) include benzoic acid, benzoyl halide, and compounds including one or more of these and in which one or more substituent groups are present on one or more carbon atoms. Examples of the substituent groups on one or more carbon atoms include the fluorinated hydrocarbon structural moiety (F), aliphatic hydrocarbon groups, alkoxy groups, halogen atoms, aryl groups, aryloxy groups, and aralkyl groups. Specific examples of these are as described above. These may be used alone or in a combination of two or more.

These active ester compounds can be produced by, for example, mixing and stirring reaction raw materials at a temperature of approximately 40 to 65° C. in the presence of an alkaline catalyst. The reaction may be carried out in an organic solvent as necessary. Furthermore, after completion of the reaction, the reaction product may be purified by washing with water, reprecipitation, or the like.

Examples of the alkaline catalyst include sodium hydroxide, potassium hydroxide, triethylamine, and pyridine. These may be used alone or in a combination of two or more. Furthermore, these may be used as an approximately 3.0 to 30% aqueous solution. In particular, sodium hydroxide or potassium hydroxide, which has high catalytic activity, is preferable.

Examples of the organic solvent include ketone solvents, such as acetone, methyl ethyl ketone, and cyclohexanone; acetate ester solvents, such as ethyl acetate, butyl acetate, cellosolve acetate, propylene glycol monomethyl ether acetate, and carbitol acetate; carbitol solvents, such as cellosolve and butylcarbitol; aromatic hydrocarbon solvents, such as toluene and xylene; dimethylformamide; dimethylacetamide; and N-methylpyrrolidone. These may be used alone, or two or more of these may be used as a mixed solvent.

Although a reaction ratio between the reaction raw materials is appropriately adjusted in accordance with the desired properties and the like of the resulting active ester compound, the reaction ratio is, in particular, preferably as follows.

In the production of the active ester compound (A1), the reaction ratio between the aromatic monohydroxy compound (a1) and the aromatic polycarboxylic acid or an acid halide thereof (a2) may be as follows. 0.95 to 1.05 moles of the aromatic monohydroxy compound (a1) is present per mole of the total of carboxyl groups or acid halide groups present in the aromatic polycarboxylic acid or an acid halide thereof (a2). This is preferable because, with this ratio, the target active ester compound (A1) can be obtained in high yield.

In the production of the active ester compound (A2), the reaction ratio of the esterification product between the compound containing two or more phenolic hydroxyl groups in the structure of the molecule (a3) and the aromatic monocarboxylic acid or an acid halide thereof (a4) may be as follows. 0.95 to 1.05 moles of the aromatic monocarboxylic acid or an acid halide thereof (a4) is present per mole of the total of phenolic hydroxyl groups present in the compound containing two or more phenolic hydroxyl groups in the structure of the molecule (a3). This is preferable because, with this ratio, the target active ester compound (A2) can be obtained in high yield.

In the production of the active ester compound (A3), the reaction ratio between the aromatic monohydroxy compound (a1), the aromatic polycarboxylic acid or an acid halide thereof (a2), and the compound containing two or more phenolic hydroxyl groups in the structure of the molecule (a3) may be as follows. The ratio between the number of moles of the hydroxyl groups present in the aromatic monohydroxy compound (a1) and the number of moles of the hydroxyl groups present in the compound containing two or more phenolic hydroxyl groups in the structure of the molecule (a3) is preferably 10:90 to 75:25 and more preferably 20:80 to 60:40. Furthermore, it is preferable that the total of hydroxyl groups present in the aromatic monohydroxy compound (a1) and hydroxyl groups present in the compound containing two or more phenolic hydroxyl groups in the structure of the molecule (a3) be within a range of 0.9 to 1.1 moles per mole of the total of carboxyl groups or acid halide groups present in the aromatic polycarboxylic acid or an acid halide thereof (a2).

In the production of the active ester compound (A4), the reaction ratio between the aromatic polycarboxylic acid or an acid halide thereof (a2), the compound containing two or more phenolic hydroxyl groups in the structure of the molecule (a3), and the aromatic monocarboxylic acid or an acid halide thereof (a4) may be as follows. The ratio of the total of carboxyl groups or the acid halide groups present in the aromatic polycarboxylic acid or an acid halide thereof (a2) is preferably within a range of 0.5 to 5 moles and more preferably within a range of 0.8 to 3 moles, per mole of the total of carboxyl groups or acid halide groups present in the aromatic monocarboxylic acid or an acid halide thereof (a4). Furthermore, it is preferable that the total of carboxyl groups or acid halide groups present in the aromatic polycarboxylic acid or an acid halide thereof (a2) and carboxyl groups or acid halide groups present in the aromatic monocarboxylic acid or an acid halide thereof (a4) be within a range of 0.9 to 1.1 per mole of the hydroxyl groups present in the compound containing two or more phenolic hydroxyl groups in the structure of the molecule (a3).

It is preferable that the active ester compounds (A1) and (A2) have a melt viscosity at 150° C. within a range of 0.01 to 5 dPa·s. Note that in the present invention, the melt viscosity at 150° C. is the value measured with an ICI viscometer in accordance with ASTM D 4287.

The active ester compounds (A3) and (A4) preferably have a softening point within a range of 40 to 200° C. and more preferably within a range of 50 to 180° C., as measured in accordance with JIS K 7234. Furthermore, in terms of achieving excellent curability and forming a cured product having an excellent balance between various properties, it is preferable that the compounds have a functional group equivalent weight within a range of 150 to 350 g/equivalent. Note that in the present invention, the phrase "functional group in the active ester compound" refers to a moiety containing an ester linkage in the active ester compound and to a phenolic hydroxyl group in the active ester compound. Furthermore, the functional group equivalent weight of the active ester compound is the value calculated from the amounts of the reaction raw materials prepared.

The active ester compound of the present invention has an acid value and a hydroxyl value that are each preferably less than or equal to 10 mg KOH/g and more preferably less than or equal to 5 mg KOH/g. With such an acid value and a hydroxyl value, the active ester compound can form a cured product having an excellent balance between dielectric properties, copper foil adhesion properties, and various other properties.

The active ester compound of the present invention has an acid value and a hydroxyl value that are each preferably less than or equal to 10 mg KOH/g and more preferably less than or equal to 5 mg KOH/g. With such an acid value and a hydroxyl value, the active ester compound can form a cured product having an excellent balance between dielectric properties, copper foil adhesion properties, and various other properties.

The active ester compound of the present invention has an elemental fluorine content preferably within a range of 5 to 40 mass % and more preferably within a range of 10 to 30 mass %. With such an elemental fluorine content, the active ester compound can form a cured product having an excellent balance between dielectric properties, copper foil adhesion properties, and various other properties. The elemental fluorine content is calculated based on the raw materials and the ratio between the raw materials that are selected in the designing of the resin. Also, the elemental fluorine content can be actually measured by combustion ion chromatography. In the present invention, it is preferable that the latter, that is, the actual measured value, be within the ranges mentioned above.

The active ester compound of the present invention may be used in combination with an active ester compound that contains no fluorinated hydrocarbon structural moiety (F). In this case, the elemental fluorine content relative to the combined amount of the two compounds is preferably within the range of 5 to 40 mass % and more preferably within the range of 10 to 30 mass %.

According to the present invention, a curable composition includes the active ester compound and a curing agent. It is sufficient that the curing agent be a compound that can react with the active ester compound of the present invention, and therefore, various compounds may be used without particular limitations. Examples of the curing agent include epoxy resins. Examples of the epoxy resins include a polyglycidyl ether of the compound containing two or more phenolic hydroxyl groups in the structure of the molecule (a3).

In the curable composition of the present invention, the mixing ratio between the active ester compound and the curing agent is not particularly limited and may be appropriately adjusted in accordance with the desired cured product properties or the like. In the case where an epoxy resin is used as a curing agent, an exemplary formulation is as follows. Preferably, the ratio is such that the total of functional groups in the active ester compound is 0.7 to 1.5 moles per mole of the total of epoxy groups in the epoxy resin.

In the case where an epoxy resin is used as a curing agent, another curing agent that is typically used as a curing agent for epoxy resins as well as for the active ester compound of the present invention may be used in combination. Examples of such a curing agent include phenolic resins, amine compounds, and acid anhydrides. In the case where such a curing agent is used, the mixing ratio is not particularly limited, but preferably, the elemental fluorine content in the epoxy resin curing agent that includes the active ester compound of the present invention be within the range of 5 to 40 mass % and more preferably within the range of 10 to 30 mass %.

The curable composition of the present invention may further include a curing accelerator. Examples of the curing accelerator include phosphorus compounds, tertiary amines, imidazole compounds, pyridine compounds, metal salts of an organic acid, Lewis acids, and amine complex salts. In particular, in terms of achieving excellent curability, thermal resistance, dielectric properties, moisture absorption resistance, and the like, a preferred phosphorus compound is triphenylphosphine, a preferred tertiary amine is 1,8-diazabicyclo[5.4.0]-undecene (DBU), a preferred imidazole compound is 2-ethyl-4-methylimidazole, and preferred pyridine compounds are 4-dimethylaminopyridine and 2-phenylimidazole. It is preferable that the amount of addition of the curing accelerator be within a range of 0.01 to 15 mass % based on 100 parts by mass of the curable composition.

The curable composition of the present invention may further include one or more other resin components. Examples of the one or more other resin components include phenolic hydroxyl group-containing compounds, such as the compound containing two or more phenolic hydroxyl groups in the structure of the molecule (a3); amine compounds, such as diaminodiphenylmethane, diethylenetriamine, triethylenetetramine, diaminodiphenyl sulfone, isophoronediamine, imidazole, $BF_3$-amine complexes, and guanidine derivatives; amide compounds, such as dicyandiamide, and a polyamide resin synthesized from a linolenic acid dimer and ethylenediamine; benzoxazine compounds; cyanate ester resins; bismaleimide resins; styrene-maleic anhydride resins; allyl group-containing resins typified by diallylbisphenol and triallyl isocyanurate; polyphosphate esters and phosphate ester-carbonate copolymers; and poly (fluoroalkylene) resins, which are polymers including, as an essential monomer component, a fluoroalkylene compound, such as tetrafluoroethylene, trifluoropropene, or hexafluoropropylene. These may be used alone or in a combination of two or more. In particular, a poly(fluoroalkylene) resin is preferable in terms of providing a curable composition that can form a cured product having enhanced dielectric properties and copper foil adhesion properties.

The mixing ratio of the one or more other resin components is not particularly limited and may be appropriately adjusted in accordance with the desired cured product properties or the like. An exemplary mixing ratio is preferably such that the one or more other resin components be used in an amount ranging from 1 to 50 mass % relative to the resin solids content of the curable composition of the present invention. Note that the resin solids content of the curable composition is a content of the non-solvent components of the curable composition.

The curable composition of the present invention may include, as necessary, any of a variety of additives, examples of which include flame retardants, inorganic fillers, silane coupling agents, release agents, pigments, and emulsifiers.

Examples of the flame retardants include red phosphorus, ammonium phosphates, such as monoammonium phosphate, diammonium phosphate, triammonium phosphate, and ammonium polyphosphates, and inorganic phosphorus compounds such as phosphoric acid amides; phosphate ester compounds, phosphonic acid compounds, phosphinic acid compounds, phosphine oxide compounds, phosphorane compounds, nitrogen-containing organophosphorus compounds, cyclic organophosphorus compounds, such as 9,10-dihydro-9-oxa-10-phosphaphenanthrene-10-oxide, 10-(2,5-dihydroxyphenyl)-10H-9-oxa-10-phosphaphenanthrene-10-oxide, and 10-(2,7-dihydroxynaphthyl)-10H-9-oxa-10-phosphaphenanthrene-10-oxide, and organophosphorus compounds such as derivatives obtained by reacting any of the cyclic organophosphorus compounds with a compound such as an epoxy resin or a phenolic resin; nitrogen-based flame retardants, such as triazine compounds, cyanuric acid compounds, isocyanuric acid compounds, and phenothiazines; silicone-based flame retardants, such as silicone oils, silicone rubbers, and silicone resins; and inorganic flame retardants such as metal hydroxides, metal oxides, metal carbonate salt compounds, metal powders, boron compounds, and low-melting-point glass. In the case where any of the flame retardants is used, it is preferable that the flame retardant be present in an amount ranging from 0.1 to 20 mass % of the curable composition.

For example, in cases where the curable composition of the present invention is used in semiconductor encapsulating material applications, an inorganic filler is included. Examples of the inorganic filler include fused silica, crystalline silica, alumina, silicon nitride, and aluminum hydroxide. In particular, fused silica is preferable because an increased amount of the inorganic filler can be included. The fused silica may be in a pulverized form or in a spherical form. However, to increase the fused silica content and inhibit an increase in the melt viscosity of the curable composition, it is preferable to mainly use spherical fused silica. In addition, to increase the content of spherical silica, it is preferable to appropriately adjust the particle size distribution of spherical silica. The filling ratio is preferably such that the fused silica be included in an amount ranging from 0.5 to 95 parts by mass per 100 parts by mass of the curable composition.

Further, in cases where the curable composition of the present invention is used in, for example, electrically conductive paste applications, an electrically conductive filler, such as a silver powder or a copper powder may be used.

The active ester compound of the present invention and the curable composition including the active ester compound have high curability and realize excellent cured product properties in terms of, for example, dielectric properties, thermal resistance, and moisture absorption resistance. In addition, properties generally required of resin materials, such as solubility in a general-purpose organic solvent and storage stability, are sufficiently high. Accordingly, the active ester compound and the curable composition can be used widely, not only in electronic materials applications for semiconductor encapsulating materials, printed wiring boards, resist materials, and the like but also in, for example, paint, adhesive, and molded article applications.

In the case where the curable composition of the present invention is used in semiconductor encapsulating material applications, it is generally preferable that an inorganic filler be included. The semiconductor encapsulating material can be prepared by, for example, mixing the mixture ingredients by using an extrusion apparatus, a kneader, a roller, or the like. A method for forming a semiconductor package by using the obtained semiconductor encapsulating material is as follows, for example. The semiconductor encapsulating material is molded by using a casting mold, a transfer molding apparatus, an injection molding apparatus, or the like and is then heated at a temperature of 50 to 200° C. for 2 to 10 hours. With such a method, a semiconductor device, which is a molded article, can be obtained.

In the case where the curable composition of the present invention is used in printed wiring board applications or in build-up adhesive film applications, it is generally preferable to dilute the curable composition for use by adding an organic solvent. Examples of the organic solvent include methyl ethyl ketone, acetone, dimethylformamide, methyl isobutyl ketone, methoxy propanol, cyclohexanone, methyl cellosolve, ethyl diglycol acetate, and propylene glycol monomethyl ether acetate. The type and the content of the organic solvent may be appropriately adjusted in accordance with the environment in which the curable composition is used. For example, for printed wiring board applications, a polar solvent having a boiling point lower than or equal to 160° C., such as methyl ethyl ketone, acetone, or dimethylformamide, is preferable, and it is preferable that the solvent be used in a ratio such that the non-volatile content is 40 to 80 mass %. For build-up adhesive film applications, examples of preferred solvents that may be used include ketone solvents, such as acetone, methyl ethyl ketone, and cyclohexanone; acetate ester solvents, such as ethyl acetate, butyl acetate, cellosolve acetate, propylene glycol monomethyl ether acetate, and carbitol acetate; carbitol solvents, such as cellosolve and butylcarbitol; aromatic hydrocarbon solvents, such as, toluene and xylene; dimethylformamide; dimethylacetamide; and N-methylpyrrolidone. It is preferable that the solvent be used in a ratio such that the non-volatile content is 30 to 60 mass %.

Furthermore, a method for producing a printed wiring board by using the curable composition of the present invention may be, for example, a method in which a reinforcing substrate is impregnated with the curable composition and cured, thereby obtaining a prepreg, and the prepreg and a copper foil are stacked on top of each other and are subjected to thermocompression bonding. Examples of the reinforcing substrate include paper, glass fabrics, nonwoven glass fabrics, aramid paper, aramid fabrics, glass mats, and glass roving fabrics. The amount of the curable composition for impregnation is not particularly limited, but in general, it is preferable that the preparation is made such that the resin content of the prepreg is 20 to 60 mass %.

EXAMPLES

The present invention will now be described in more detail with reference to Examples and a Comparative Example. In the examples, "parts" and "%" are on a mass basis unless otherwise specified.

In the examples, GPC measurement conditions are as follows.

Measurement instrument: HLC-8220 GPC, manufactured by Tosoh Corporation

Column: HXL-L guard column, manufactured by Tosoh Corporation

+TSK-GEL G2000HXL, manufactured by Tosoh Corporation

+TSK-GEL G2000HXL, manufactured by Tosoh Corporation

+TSK-GEL G3000HXL, manufactured by Tosoh Corporation

+TSK-GEL G4000HXL, manufactured by Tosoh Corporation

Detector: RI (Differential Refractometer)

Data processing: GPC-8020 Model II Version 4.10, manufactured by Tosoh Corporation Measurement Conditions:

Column temperature 40° C.

Developing solvent tetrahydrofuran

Flow rate 1.0 ml/min

Standard: The following monodisperse polystyrenes, whose molecular weights are known, were used in accordance with the measurement manual of GPC-8020 Model II version 4.10

(Polystyrenes Used)

A-500, manufactured by Tosoh Corporation

A-1000, manufactured by Tosoh Corporation

A-2500, manufactured by Tosoh Corporation

A-5000, manufactured by Tosoh Corporation

F-1, manufactured by Tosoh Corporation

F-2, manufactured by Tosoh Corporation

F-4, manufactured by Tosoh Corporation

F-10, manufactured by Tosoh Corporation

F-20, manufactured by Tosoh Corporation

F-40, manufactured by Tosoh Corporation

F-80, manufactured by Tosoh Corporation

F-128, manufactured by Tosoh Corporation

Sample: a solution (50 µl) obtained by filtering a 1.0 mass % (on a resin solids basis) tetrahydrofuran solution through a microfilter Example 1: Production of Active Ester Compound (1)

A flask equipped with a thermometer, a dropping funnel, a condenser tube, a fractionating column, and a stirrer was charged with 144 g of 1-naphthol, 168 g of bisphenol AF, 203 g of isophthalic acid chloride, and 1500 g of toluene, and these were dissolved while the interior of the system was purged with nitrogen under reduced pressure. 0.7 g of tetrabutylammonium bromide was dissolved, and 412 g of a 20% aqueous solution of sodium hydroxide was added dropwise over 3 hours while nitrogen gas purging was performed with the temperature of the interior of the system being controlled not to exceed 60° C. After completion of the dropwise addition, the stirring was continued for another 1 hour. The reacted mixture was allowed to settle so that the liquid phases were separated from each other, and then the aqueous layer was removed. 440 g of water was added to the remaining organic layer, and these were mixed together with stirring for approximately 15 minutes. The product was allowed to settle so that the liquid phases were separated from each other, and then the aqueous layer was removed. This operation was repeated until the pH of the aqueous layer reached 7. Subsequently, the product was dried by heating under reduced pressure to obtain 340 g of an active ester compound (1). In the active ester compound (1), the functional group equivalent weight was 221 g/equivalent, the elemental fluorine content was 12.9 mass %, and the softening point was 121° C., as measured in accordance with JIS K 7234. A GPC chart of the active ester compound (1) is shown in FIG. 1.

Example 2: Production of Active Ester Compound (2)

Figure 2:
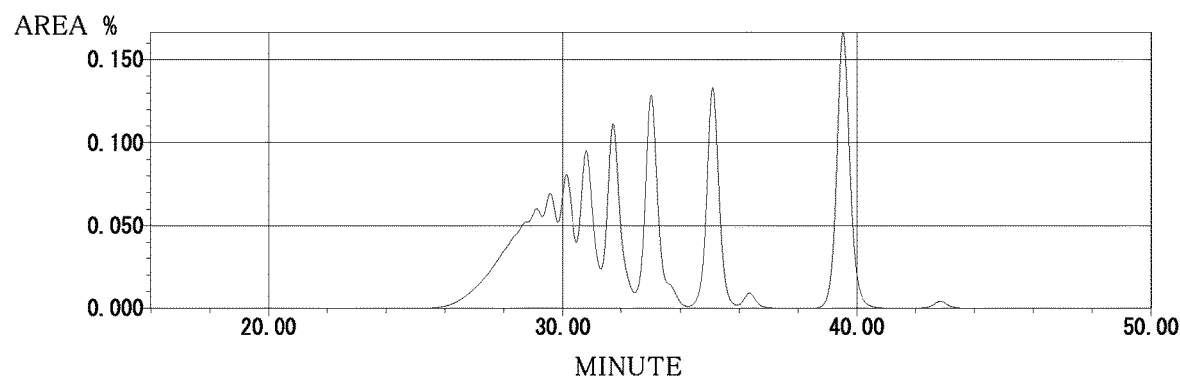
FIG. 2 is a GPC chart of an active ester compound (2), which was obtained in Example 2.

A flask equipped with a thermometer, a dropping funnel, a condenser tube, a fractionating column, and a stirrer was charged with 86 g of 1-naphthol, 202 g of bisphenol AF, 182 g of isophthalic acid chloride, and 1200 g of toluene, and these were dissolved while the interior of the system was purged with nitrogen under reduced pressure. 0.6 g of tetrabutylammonium bromide was dissolved, and 371 g of a 20% aqueous solution of sodium hydroxide was added dropwise over 3 hours while nitrogen gas purging was performed with the temperature of the interior of the system being controlled not to exceed 60° C. After completion of the dropwise addition, the stirring was continued for another 1 hour. The reacted mixture was allowed to settle so that the liquid phases were separated from each other, and then the aqueous layer was removed. 400 g of water was added to the remaining organic layer, and these were mixed together with stirring for approximately 15 minutes. The product was allowed to settle so that the liquid phases were separated from each other, and then the aqueous layer was removed. This operation was repeated until the pH of the aqueous layer reached 7. Subsequently, the product was dried by heating under reduced pressure to obtain 400 g of an active ester compound (2). In the active ester compound (2), the functional group equivalent weight was 225 g/equivalent, the elemental fluorine content was 16.9 mass %, and the softening point was 140° C., as measured in accordance with JIS K 7234. A GPC chart of the active ester compound (2) is shown in FIG. 2.

Example 3: Production of Active Ester Compound (3)

Figure 3:
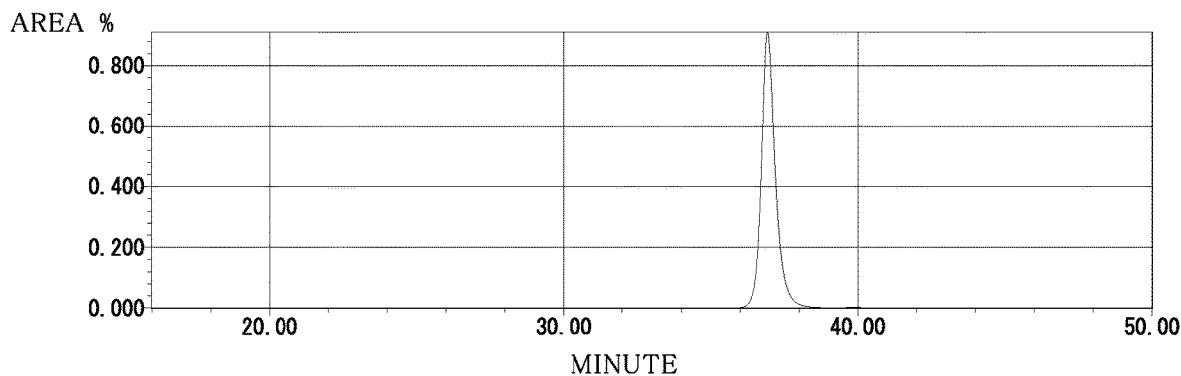
FIG. 3 is a GPC chart of an active ester compound (3), which was obtained in Example 3.

A flask equipped with a thermometer, a dropping funnel, a condenser tube, a fractionating column, and a stirrer was charged with 168 g of bisphenol AF, 141 g of benzoyl chloride, and 800 g of toluene, and these were dissolved while the interior of the system was purged with nitrogen under reduced pressure. 0.4 g of tetrabutylammonium bromide was dissolved, and 206 g of a 20% aqueous solution of sodium hydroxide was added dropwise over 3 hours while nitrogen gas purging was performed with the temperature of the interior of the system being controlled not to exceed 60° C. After completion of the dropwise addition, the stirring was continued for another 1 hour. The reacted mixture was allowed to settle so that the liquid phases were separated from each other, and then the aqueous layer was removed. 270 g of water was added to the remaining organic layer, and these were mixed together with stirring for approximately 15 minutes. The product was allowed to settle so that the liquid phases were separated from each other, and then the aqueous layer was removed. This operation was repeated until the pH of the aqueous layer reached 7. Subsequently, the product was dried by heating under reduced pressure to obtain 270 g of an active ester compound (3). In the active ester compound (3), the functional group equivalent weight was 272 g/equivalent, the elemental fluorine content was 20.9 mass %, and the softening point was 61° C., as measured in accordance with JIS K 7234. A GPC chart of the active ester compound (3) is shown in FIG. 3.

Example 4: Production of Active Ester Compound (4)

Figure 4:
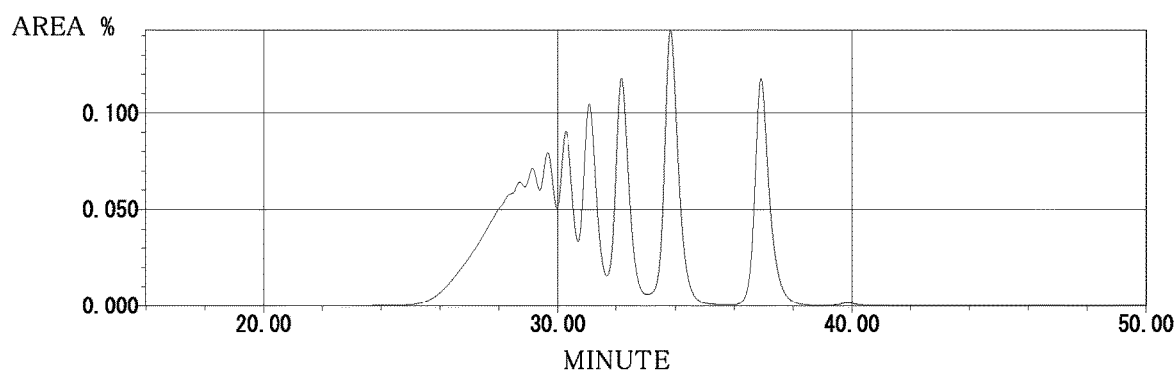
FIG. 4 is a GPC chart of an active ester compound (4), which was obtained in Example 4.

A flask equipped with a thermometer, a dropping funnel, a condenser tube, a fractionating column, and a stirrer was charged with 182 g of bisphenol AF, 73 g of isophthalic acid chloride, 51 g of benzoyl chloride, and 800 g of toluene, and these were dissolved while the interior of the system was purged with nitrogen under reduced pressure. 0.4 g of tetrabutylammonium bromide was dissolved, and 223 g of a 20% aqueous solution of sodium hydroxide was added dropwise over 3 hours while nitrogen gas purging was performed with the temperature of the interior of the system being controlled not to exceed 60° C. After completion of the dropwise addition, the stirring was continued for another 1 hour. The reacted mixture was allowed to settle so that the liquid phases were separated from each other, and then the aqueous layer was removed. 270 g of water was added to the remaining organic layer, and these were mixed together with stirring for approximately 15 minutes. The product was allowed to settle so that the liquid phases were separated from each other, and then the aqueous layer was removed. This operation was repeated until the pH of the aqueous layer reached 7. Subsequently, the product was dried by heating under reduced pressure to obtain 265 g of an active ester compound (4). In the active ester compound (4), the functional group equivalent weight was 246 g/equivalent, the elemental fluorine content was 23.2 mass %, and the softening point was 145° C., as measured in accordance with JIS K 7234. A GPC chart of the active ester compound (4) is shown in FIG. 4.

Production Example 1: Production of Active Ester Compound (5)

A flask equipped with a thermometer, a dropping funnel, a condenser tube, a fractionating column, and a stirrer was charged with 72 g of 1-naphthol, 165 g of a dicyclopentadiene adduct type of phenolic resin (J-DPP-85, manufactured by JFE Chemical Corporation; softening point, 86° C.; and hydroxyl group equivalent weight, 165 g/equivalent), 152 g of isophthalic acid chloride, and 1000 g of toluene, and these were dissolved while the interior of the system was purged with nitrogen under reduced pressure. 0.5 g of tetrabutylammonium bromide was dissolved, and 310 g of a 20% aqueous solution of sodium hydroxide was added dropwise over 3 hours while nitrogen gas purging was performed with the temperature of the interior of the system being controlled not to exceed 60° C. After completion of the dropwise addition, the stirring was continued for another 1 hour. The reacted mixture was allowed to settle so that the liquid phases were separated from each other, and then the aqueous layer was removed. 330 g of water was added to the remaining organic layer, and these were mixed together with stirring for approximately 15 minutes. The product was allowed to settle so that the liquid phases were separated from each other, and then the aqueous layer was removed. This operation was repeated until the pH of the aqueous layer reached 7. Subsequently, the product was dried by heating under reduced pressure to obtain 330 g of an active ester compound (5). In the active ester compound (5), the functional group equivalent weight was 223 g/equivalent, and the softening point was 150° C., as measured in accordance with JIS K 7234.

Further, the following compounds were used in the examples of the present application and the comparative example.

Epoxy resin: HP-7200H, manufactured by DIC Corporation, which is a dicyclopentadiene-type epoxy resin having an epoxy group equivalent weight of 275 g/equivalent Polytetrafluoroethylene dispersion liquid: MPT-M11, manufactured by Mitsubishi Pencil Co., Ltd., which is a dispersion liquid containing polytetrafluoroethylene dispersed in methyl ethyl ketone and having a non-volatile content of 30 mass %

Examples 5 to 8 and Comparative Example 1

Curable compositions were adjusted in the manner described below, and various evaluation tests were conducted. The results are shown in Table 1.

Production of Curable Composition

The epoxy resin and the active ester compound were prepared according to the formulation shown in Table 1 below and were dissolved in methyl ethyl ketone that was added. Next, the polytetrafluoroethylene dispersion liquid was added such that the amount of polytetrafluoroethylene was 10 mass % relative to the resin solids content of the curable composition. Furthermore, 0.2 mass % of dimethylaminopyridine, relative to the resin solids content of the curable composition, was added, and the non-volatile content was adjusted to 58 mass % by using methyl ethyl ketone. In this manner, curable compositions were obtained. The obtained curable compositions were subjected to various evaluation tests, which were conducted in the manners described below. The results are shown in Table 1.

Storage Stability of Curable Composition

Immediately after production, the curable composition was left to stand at room temperature (25° C.) to measure the amount of time that elapsed before agglomeration of polytetrafluoroethylene was observed.

Preparation of Multilayer Sheet

A multilayer sheet was prepared under the following conditions.
Substrate: glass cloth #2116 (210×280 mm) manufactured by Nitto Boseki Co., Ltd.

was stored for 24 hours in a room having a temperature of 23° C. and a humidity of 50%. Thereafter, a dielectric constant and a dielectric loss tangent at 1 GHz of the test piece were measured in accordance with JIS C 6481 by using an HP4291B impedance material analyzer, manufactured by Agilent Technologies, Inc.

Evaluation of Copper Foil Adhesion Properties

A test piece having a width of 10 mm and a length of 200 mm was cut from the multilayer sheet. An adhesion property of the test piece with respect to a copper foil was measured in accordance with JIS 6911.

TABLE 1

|  | Example 5 | Example 6 | Example 7 | Example 8 | Comparative Example 1 |
|---|---|---|---|---|---|
| Epoxy resin [parts by mass] | 55.4 | 55.0 | 50.2 | 54.0 | 55.2 |
| Active ester compound (1) [parts by mass] | 44.6 | | | | |
| Active ester compound (2) [parts by mass] | | 45.0 | | | |
| Active ester compound (3) [parts by mass] | | | 24.9 | | |
| Active ester compound (4) [parts by mass] | | | | 46.0 | |
| Active ester compound (5) [parts by mass] | | | 24.9 | | 44.8 |
| Storage stability (h) | No agglomeration after 48 h | No agglomeration after 48 h | No agglomeration after 48 h | No agglomeration after 48 h | Agglomeration formed after 1 h |
| Glass transition temperature (Tg) | 175 | 173 | 170 | 174 | 175 |
| Dielectric constant | 3.6 | 3.6 | 3.7 | 3.7 | 3.7 |
| Dielectric loss tangent | 0.005 | 0.005 | 0.006 | 0.006 | 0.009 |
| Adhesion property (kN/m) | 1.1 | 1.1 | 0.9 | 1.0 | 0.5 |

Copper foil: JTC foil (18 μm), manufactured by Jx Nippon Mining & Metals Corporation
Number of plies: 6
Prepreg formation condition: 160° C.
Curing conditions: 200° C., 2.0 MPa, and 1.5 hours
Sheet thickness after forming: 0.8 mm Measurement of Glass Transition Temperature (Tg)

From the obtained multilayer sheet, portions of the copper foil were etched away, and a piece having a width of 5 mm and a length of 55 mm was cut, which was used as a test piece. By using a DMS-6100 viscoelasticity measuring instrument, manufactured by SII NanoTechnology Inc., an evaluation was conducted by determining the glass transition temperature as the temperature at which the rate of change in the elastic modulus is the greatest (rate of change in tan δ is the greatest). The measurement conditions included the following: a rectangular tension method; a frequency of 1 Hz; and a heating rate of 3° C./min.

Measurement of Dielectric Constant and Dielectric Loss Tangent

From the obtained multilayer sheet, portions of the copper foil were etched away, and a piece having a width of 1.5 mm and a length of 100 mm was cut, which was used as a test piece. After being heated and vacuum-dried, the test piece

The invention claimed is:

1. An active ester compound comprising:
    a fluorinated hydrocarbon structural moiety (F) and a plurality of aromatic ester structural moieties (E) in a structure of a molecule; and
    an aryloxycarbonyl structure (P) or an arylcarbonyloxy structure (A) at an end of the molecule,
    wherein the active ester compound is an esterification product of a compound (a1), a compound (a2), and a compound (a3), and at least one of the compound (a1), the compound (a2), and the compound (a3) contains the fluorinated hydrocarbon structural moiety (F) in a structure of a molecule, the compound (a1) being an aromatic monohydroxy compound, the compound (a2) being an aromatic polycarboxylic acid or an acid halide thereof (a2), the compound (a3) being a compound containing at least two phenolic hydroxyl groups in a structure of a molecule; and
    the ratio between the number of moles of the hydroxyl groups present in the aromatic monohydroxy compound (a1) and the number of moles of the hydroxyl groups present in the compound containing two or more phenolic hydroxyl groups in the structure of the molecule (a3) is 10:90 to 75:25.

2. The active ester compound according to claim 1, wherein the fluorinated hydrocarbon structural moiety (F) is a perfluoroalkyl group having 1 to 6 carbon atoms.

3. A curable composition comprising the active ester compound according to claim 1 and a curing agent.

4. The active ester compound according to claim 1, wherein the compound (a1) is a substituted or unsubstituted naphthol compound.

5. The curable composition according to claim 3, further comprising a poly(fluoroalkylene) resin.

6. A cured product of the curable composition according to claim 5.

7. A semiconductor encapsulating material comprising the curable composition according to claim 5.

8. A printed wiring board comprising a product of the curable composition according to claim 5.

9. A build-up film comprising a product of the curable composition according to claim 5.

* * * * *